(12) United States Patent
Dixit et al.

(10) Patent No.: US 10,117,831 B2
(45) Date of Patent: Nov. 6, 2018

(54) SOFT CHEW PHARMACEUTICAL FORMULATIONS

(71) Applicant: First Time US Generics LLC, Broomall, PA (US)

(72) Inventors: Manesh A. Dixit, Broomall, PA (US); Vaibhav L. Pawar, Broomall, PA (US); Rushi R. Patel, Broomall, PA (US); Mineshkumar D. Patel, Broomall, PA (US); Amol Somwanshi, Navi Mumbai (IN)

(73) Assignee: First Time US Generics LLC, Broomall, PA (US)

( * ) Notice: Subject to any disclaimer, the term of this patent is extended or adjusted under 35 U.S.C. 154(b) by 0 days.

(21) Appl. No.: 15/629,354

(22) Filed: Jun. 21, 2017

(65) Prior Publication Data
US 2018/0169008 A1    Jun. 21, 2018

Related U.S. Application Data

(63) Continuation-in-part of application No. PCT/US2016/067443, filed on Dec. 19, 2016.

(51) Int. Cl.
| | |
|---|---|
| *A61K 9/00* | (2006.01) |
| *A61K 31/00* | (2006.01) |
| *A61K 9/20* | (2006.01) |
| *A61K 31/405* | (2006.01) |
| *A61K 31/546* | (2006.01) |
| *A61K 31/496* | (2006.01) |
| *A61K 31/501* | (2006.01) |
| *A61K 31/635* | (2006.01) |

(52) U.S. Cl.
CPC .......... *A61K 9/0056* (2013.01); *A61K 9/2013* (2013.01); *A61K 9/2031* (2013.01); *A61K 9/2054* (2013.01); *A61K 9/2059* (2013.01); *A61K 9/2095* (2013.01); *A61K 31/405* (2013.01); *A61K 31/496* (2013.01); *A61K 31/501* (2013.01); *A61K 31/546* (2013.01); *A61K 31/635* (2013.01)

(58) Field of Classification Search
CPC .. A61K 9/0056; A61K 9/2013; A61K 9/2031; A61K 9/2054; A61K 9/2059; A61K 9/2095; A61K 31/405; A61K 31/496; A61K 31/501; A61K 31/546; A61K 31/635
See application file for complete search history.

(56) References Cited

U.S. PATENT DOCUMENTS

| | | |
|---|---|---|
| 4,327,076 A | 4/1982 | Puglia |
| 4,327,077 A | 4/1982 | Puglia |
| 4,582,709 A | 4/1986 | Peters |
| 4,882,161 A | 11/1989 | Scheurer |
| 5,380,535 A | 1/1995 | Geyer |
| 5,576,014 A | 11/1996 | Mizumoto |
| 5,599,577 A | 2/1997 | Stevens |
| 5,637,313 A | 6/1997 | Chau |
| 5,679,376 A | 10/1997 | Stevens |
| 5,817,340 A | 10/1998 | Roche |
| 5,840,334 A | 11/1998 | Raiden |
| 5,853,758 A | 12/1998 | Lo |
| 6,270,790 B1 | 8/2001 | Robinson |
| 6,432,442 B1 | 8/2002 | Buchler |
| 6,471,991 B2 | 10/2002 | Robinson |
| 6,495,177 B1 | 12/2002 | deVries |
| 6,517,886 B1 | 2/2003 | Chau |
| 6,814,978 B2 | 11/2004 | Bunick |
| 7,029,699 B2 | 4/2006 | Robinson |
| 7,914,811 B2 | 3/2011 | Bunick |
| 7,955,632 B2 | 6/2011 | Paulsen |
| 8,114,455 B2 | 2/2012 | Paulsen |
| 8,293,265 B2 | 10/2012 | Paulsen |
| 8,496,969 B2 | 7/2013 | Wynn |
| 8,512,787 B2 | 8/2013 | Paulsen |
| 8,758,814 B2 | 6/2014 | Shah |
| 8,807,979 B2 | 8/2014 | Sowden |
| 8,865,240 B2 | 10/2014 | Paulsen |
| 9,107,807 B2 | 8/2015 | Sowden |
| 9,808,011 B2 | 11/2017 | Coleman |
| 2001/0043947 A1 | 11/2001 | Robinson |
| 2002/0122822 A1 | 9/2002 | Bunick |
| 2003/0049316 A1 | 3/2003 | Robinson |
| 2003/0175336 A1 | 9/2003 | Luber |
| 2003/0175339 A1 | 9/2003 | Bunick |
| 2004/0109889 A1 | 6/2004 | Bunick |
| 2004/0241208 A1 | 12/2004 | Sowden |
| 2004/0265372 A1 | 12/2004 | Wynn |
| 2004/0265373 A1 | 12/2004 | Wynn |
| 2005/0158383 A1 | 7/2005 | Boehm |

(Continued)

FOREIGN PATENT DOCUMENTS

| | | |
|---|---|---|
| EP | 1924151 B1 | 9/2014 |
| WO | 93/13758 A1 | 7/1993 |

(Continued)

OTHER PUBLICATIONS

Patent Cooperation Treaty, Written Opinion of International Search Authority, Application PCT/US2016/067443, dated Mar. 27, 2017.

(Continued)

*Primary Examiner* — Robert A Wax
*Assistant Examiner* — Olga V Tcherkasskaya
(74) *Attorney, Agent, or Firm* — William Charles West

(57) ABSTRACT

A product and process of manufacturing an edible soft-chewable dosage form for the delivery of pharmaceutically active ingredients or nutritional agents orally to an animal or human subject, by forming a granulated soft-chew mass by appropriate mixing and sifting steps, and forming tablets with a compression press. Such soft-chew dosage forms have hardness of less than about 2 kilopond and friability of less than about 1% at 300 rotations (per USP). The process for manufacturing such compressed soft-chew tablets employs compression (tablet) pressing equipment to produce soft-chew tablets of consistent weight and texture.

2 Claims, 4 Drawing Sheets

(56) References Cited

U.S. PATENT DOCUMENTS

| | | |
|---|---|---|
| 2006/0039967 A1 | 2/2006 | Ohta |
| 2006/0121092 A1 | 6/2006 | Ream |
| 2006/0121093 A1 | 6/2006 | Ream |
| 2006/0141009 A1 | 6/2006 | Huron |
| 2007/0128251 A1 | 6/2007 | Paulsen |
| 2008/0075759 A1 | 3/2008 | Paulsen |
| 2009/0214445 A1 | 8/2009 | Boghani |
| 2009/0258039 A1 | 10/2009 | Bunick |
| 2009/0280159 A1 | 11/2009 | Paulsen |
| 2010/0010101 A1 | 1/2010 | Cherukuri |
| 2010/0087492 A1 | 4/2010 | Johnson |
| 2010/0092555 A1 | 4/2010 | Wynn |
| 2010/0312652 A1 | 12/2010 | Boghani |
| 2011/0223234 A1 | 9/2011 | Paulsen |
| 2012/0009129 A1 | 1/2012 | Brzeczko |
| 2012/0039957 A1 | 2/2012 | Brzeczko |
| 2012/0141574 A1 | 6/2012 | Paulsen |
| 2013/0071476 A1 | 3/2013 | Cherukuri |
| 2013/0252979 A1 | 9/2013 | Meier |
| 2013/0330408 A1 | 12/2013 | Jacobs |
| 2013/0331348 A1 | 12/2013 | Paulsen |
| 2014/0141055 A1 | 5/2014 | Kluger |
| 2015/0224052 A1 | 8/2015 | Paulsen |
| 2015/0307504 A1 | 10/2015 | Singh |

FOREIGN PATENT DOCUMENTS

| | | |
|---|---|---|
| WO | 96/18387 A1 | 6/1996 |
| WO | 97/39747 A1 | 10/1997 |
| WO | 03/026613 A1 | 4/2003 |
| WO | 2004/014143 A1 | 2/2004 |
| WO | 2006/036552 A2 | 4/2006 |
| WO | 2006/127494 A2 | 11/2006 |
| WO | 2006/127498 A2 | 11/2006 |
| WO | 2006/127559 A2 | 11/2006 |
| WO | 2006/127616 A9 | 11/2006 |
| WO | 2006/127618 A9 | 11/2006 |
| WO | 2006/127679 A9 | 11/2006 |
| WO | 2006/127680 A9 | 11/2006 |
| WO | 2006/127681 A2 | 11/2006 |
| WO | 2006/127684 A2 | 11/2006 |
| WO | 2006/127685 A2 | 11/2006 |
| WO | 2006/127686 A2 | 11/2006 |
| WO | 2006/127689 A2 | 11/2006 |
| WO | 2006/127690 A2 | 11/2006 |
| WO | 2006/127738 A9 | 11/2006 |
| WO | 2006/127740 A2 | 11/2006 |
| WO | 2006/127741 A9 | 11/2006 |
| WO | 2006/127742 A9 | 11/2006 |
| WO | 2007/052121 A2 | 5/2007 |
| WO | 2007/055696 A1 | 5/2007 |
| WO | 2007/058644 A1 | 5/2007 |
| WO | 2007/058645 A1 | 5/2007 |
| WO | 2007/067582 A2 | 6/2007 |
| WO | 2007/005318 A2 | 1/2008 |
| WO | 2009/064859 A1 | 5/2009 |
| WO | 2010/039892 A1 | 4/2010 |
| WO | 2010/122358 A2 | 10/2010 |
| WO | 2011/079074 A1 | 6/2011 |
| WO | 2011/079248 A1 | 6/2011 |
| WO | 2012/021819 A1 | 2/2012 |
| WO | 2012/090194 A2 | 5/2012 |
| WO | 2013/004250 A1 | 1/2013 |
| WO | 2013/068371 A1 | 5/2013 |
| WO | 2014/079825 A1 | 5/2014 |

OTHER PUBLICATIONS

Patent Cooperation Treaty, International Search Report, Application PCT/US2016/067443, dated Mar. 27, 2017.
Patent Cooperation Treaty, Applicant's Informal Comments Under §7.030 of the PCT Applicant's Guide on the Written Opinion of the International Search Authority, Application PCT/US2016/067443, dated May 28, 2017.

SOFT CHEW PHARMACEUTICAL FORMULATIONS

CROSS REFERENCE TO RELATED APPLICATION

This application is a Continuation-In-Part of PCT International Patent Application PCT/US16/67443, filed Dec. 19, 2016, and claims priority to U.S. Patent Application 62/269,951, filed Dec. 19, 2015, the entire contents of which are incorporated by reference.

FIELD OF INVENTION

This invention relates products and processes for the manufacture of soft-chewable tablet pharmaceutical or nutritional dosage forms, for the oral administration of active pharmaceutical ingredients or nutritional agents.

BACKGROUND

Chewable pharmaceutical dosage units, such as chewable tablets and soft-chewable tablets, are known and have been commercialized for pediatric, geriatric and involuntary (where subject by instinct will not accept the medication meant to be swallowed e.g. animals) patient populations. Chewable tablets are also of value to competent patients as an alternative to tablets or capsules that must be swallowed whole. The formulation of a drug into a chewable dosage form can increase patient acceptance of a medication in patients that resist or are unable to swallow conventional tablets or capsules.

The texture of a chewable dosage unit form is an important factor in the acceptance of oral dosage forms by patients in need of medication. Conventional dosage forms, such as chewable compressed tablets, using conventional ingredients, can make the tablet gritty or otherwise unappealing to many patients. Soft-chewable tablet dosage units, having a soft texture, pleasant mouth feel, and palatable taste with adequate flavoring agents, provide a solution to such problems. In addition, these features can address the problem of the disagreeable taste of many active pharmaceutical ingredients. Appropriate chewable dosage forms can also address texture problems caused by dry dusty, granular, and pulverant properties of many pharmaceutical ingredients.

A soft-chewable pharmaceutical dosage unit is a solid pharmaceutical dosage unit at room temperature that has low hardness and higher moisture content than a conventional tablet or hard chewable tablet. The dosage unit may be designed to be chewed and swallowed by a human or an animal. Such a dosage unit exhibits a plastic rheological behavior and can be formed by many manufacturing processes described in prior art into many different shapes. A soft-chewable pharmaceutical dosage unit after forming should be dimensionally stable. The ingredients of such a soft-chewable pharmaceutical dosage unit may be of pharmaceutical grade.

A semi plastic oral dosage form unit has a soft texture and hardness such that the unit is intended to be chewed and swallowed. The texture of the unit is such that it does not appreciably dissolve in the mouth. A semi plastic oral dosage form unit is formed by compression on rotary tablet press and exhibits hardness of less than 2 kilopond, preferably less than 1 kilopond, and more preferably has no measurable hardness when measured with a tablet hardness tester, which has excellent flexibility, is breakage and chip resistant and yet may be easily chewed and swallowed by human or animal.

Several soft-chewable pharmaceutical dosage units are described in the prior art. For example, U.S. Pat. No. 4,327,076 describes a soft-chew antacid tablet formed by blending three—premixes and compression, but without a granulation and sifting step. The tablets have a hardness of 3 kp (col. 9, top).

For example, U.S. Pat. No. 6,387,381 discloses an extrudate formed of a matrix having starch, sugar, fat, polyhydric alcohol and water.

A process for manufacturing soft-chewable dosage form for drug delivery is described in prior art U.S. Pat. No. 6,387,381. It discloses a soft-chewable medication vehicle for drug delivery of an active ingredient to animal or human subjects, not containing ingredients of animal origin, without use of heat and without addition of water. The formed mixture was formed into individual chunks using a Formax F6™ molding machine with dies for production of chunk-like shapes, and packaged for storage.

US 2014/0141055 discloses a process using a rotary molding machine for the manufacture of semi-plastic pharmaceutical unit doses that have lower hardness and higher moisture than conventional hard chewable tablets. The disclosed rotary molding process works by displacing dough between a rotary mold roller and removal from the mold without a punch mechanism.

WO 2004/014143 discloses compositions and processes for the delivery of an additive to an organism in a form suitable for consumption, including in the form of a soft-chew composition.

US 2009/0280159 and US 2011/0223234 relate to palatable edible soft-chewable medication vehicles. The processes described in these publications relate to the problem that heat generated during the extrusion process causes deterioration in the stability of the active ingredient in the mixture.

Machines for the production of molded food patties have been described to be useful for the manufacturing of soft-chews for administration to non-human animals. Such machines are molding machines that have been originally developed for use in producing molded food products, for example the Formax F6™ molding machine made by the Formax Corporation or the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228.

The use of extruders, forming machines and rotary molding machines exhibit problems associated with the weight and physical forms of a final dosage form. Moreover, the use of such technologies may require conditioning of the final dosage form (e.g. drying or curing final formed structure) for consolidation of shape and structure of formed structure.

The use of such technologies, equipment and processes is complex, cumbersome, and something that is not traditionally used in a typical pharmaceutical oral solid dosage form manufacturing facility.

A tablet press is a mechanical device that compresses powder into tablets of uniform size and weight. A press can be used to manufacture tablets/pellets of a wide variety of materials, including pharmaceuticals, cleaning products, and cosmetics. There are two types of press machines, eccentric-type and rotary-type. The rotary-type is generally more widely used, because it facilitates high production performance with narrow weight variation along with ease of use.

Accordingly, alternate processes for manufacturing soft-chew tablet formulations on a large scale using commonly installed pharmaceutical manufacturing equipment using such as a rotary (tablet) compression press would is desirable.

SUMMARY OF THE INVENTION

The present invention overcomes the disadvantages and shortcomings of known chewable dosage forms by providing a simplified manufacturing process for soft-chewable dosage unit formulation comprising a highly palatable composition to patients, which is formed by conventional compression techniques using conventional pharmaceutical equipment, such as a rotary tablet press. Typically, conventional tablets manufactured on a rotary tablet press are formulated and processed so the tablets have a hardness of more than 10 kiloponds (kp) and any lower hardness in the art is discouraged to keep the tablet friability acceptable. But, the present inventors have found that many conventional soft-chew tablet formulations, made in the prior art using molding or extrusion techniques, can be manufactured more efficiently, reliably, and reproducibly, using a tablet press. The compressed soft-chew dosage forms of the current invention have hardness of less than 2 kp, or may have hardness of less than 1 kp, or may have no measurable hardness when tested with a conventional tablet hardness tester. Despite the low hardness, such compressed soft tablets have friability of less than 1.0%, or less than 0.5%, or less than 0.1% for 100 rotations (according to United States Pharmacopeia (USP) test <1216>); 200 rotations or 300 rotations.

The soft-chewable formulations are prepared according to methods conventional in the art, such as wet or dry granulation processes.

In one embodiment, the invention is directed to a palatable, soft-chewable pharmaceutical composition for oral administration to an involuntary subject population, for example, very young children, senile patients, or animals (i.e., for veterinary use), comprising a therapeutically effective amount of a pharmaceutically active ingredient in an immediate or controlled release form, and a palatability improving agent in an amount sufficient make the pharmaceutical composition palatable to the subject population. By the term "involuntary subject population," it is meant patients who cannot be conventionally instructed to chew and/or swallow a tablet or capsule.

An active pharmaceutical ingredient for use in the process or product according to the current invention (or active ingredient, or pharmaceutically active agent or pharmaceutically acceptable active ingredient) is a substance used in a pharmaceutical dosage form, intended to furnish pharmacological activity or to otherwise have direct effect in the diagnosis, cure, mitigation, treatment or prevention of disease, or to have direct effect in restoring, correcting or modifying physiological functions in a patient population (humans or animals).

Any pharmaceutically active ingredient or nutritional agent may be provided in the process of the invention and in the product according to the invention. Those of ordinary skill in the pharmaceutical arts will be entirely familiar with the identity of such active ingredients which may include antibiotics, analgesics, antiviral, antifungal, anti-parasitic, hormones, anti-inflammatory (including nonsteroidal anti-inflammatory), steroids, behavior modifiers, vaccines, antacids, laxatives, anticonvulsants, sedatives, tranquilizers, antitussives, antihistamines, decongestants, expectorants, appetite stimulants and suppressants, cardiovascular drugs, minerals and vitamins along with other supplement and nutraceutical agents.

DETAILED DESCRIPTION

Figure 1:
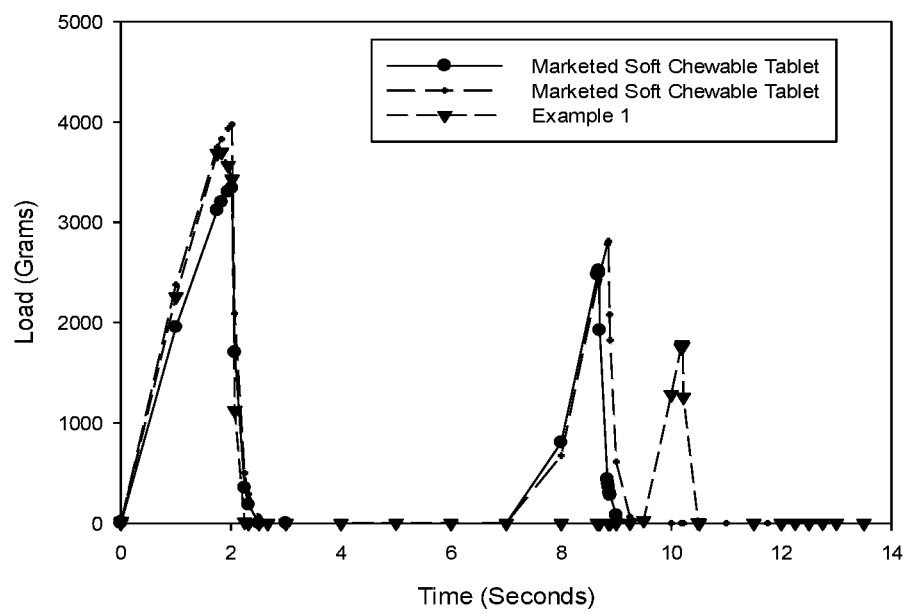
FIG. 1. Is a plot of the texture characterization and comparison to marketed soft-chewable tablet for data in Example 1, showing load peaks applied at 2, 9, and 10 seconds.

The current inventors have found that by appropriate granulation of pharmaceutical or nutritional formulations, a soft-chew composition is formed that can be pressed into soft-chew tablets using conventional tablet press equipment. This is distinguished from prior art methods for the manufacture of soft-chew tablets that require expensive and complex molding or extrusion equipment. Accordingly, this invention provides unit dosage forms for the administration of pharmaceutically active agents (drugs) or nutritional agents to humans or animals orally, wherein the dosage forms are soft-chew tablets formed by compression in a tablet press.

In an embodiment of this invention, a soft-chew mass is formed by blending appropriate active ingredients and excipients. The soft-chew mass is compressed in tablet press to provide tablets with minimal hardness, of less than or equal to about 2 kp. In an embodiment, the tablets have hardness of less than or equal to about 1 kp. In an embodiment, the tablets have no measurable hardness in a tablet hardness testing apparatus and a friability of less than about 1% at up to 300 rotations in a friability apparatus. The tablets so obtained are "soft chew" tablets.

The soft-chew mass may or may not be flowable at room temperature. In an embodiment, the soft-chew mass may not be flowable at room temperature of about 20° C. (or below). In an embodiment, the soft-chew mass may be flowable at temperatures greater than room temperature. In an embodiment, soft chew mass may be treated with heat in an equipment where, heat is applied directly to a static solid bed, directly to a moving solid bed, or directly to a fluidized solid bed to affect soft chew mass flowability.

In an embodiment, a process is provided for the manufacture of a compressed soft-chew tablet unit dosage form for the oral administration of an active pharmaceutical ingredient or a nutritional agent, in which a soft-chew tablet or semi-plastic tablet is formed by compressing a soft-chew mass on a compression press, and wherein the soft-chew tablets have a hardness of less than about 2 kp and a friability of less than about 1% at 300 rotations.

In an embodiment, a process is provided for the manufacture of a compressed soft-chew tablet unit dosage form for the oral administration of an active pharmaceutical ingredient or a nutritional agent, in which a soft-chew mass mixture is provided including an active pharmaceutical ingredient or a nutritional agent, wherein the soft-chew mass is a granulate formed with a granulation and sifting step, and wherein the soft-chew mass granulate is pressed into tablets using a tablet press, and wherein the soft-chew tablets have a hardness of less than about 2 kp and a friability of less than about 1% at 300 rotations.

In an embodiment, this invention provides a process for the manufacture of an edible compressed soft-chew tablet or semi plastic oral unit dosage form employing the steps of (a) mixing at least one active ingredient with at least one dry or liquid component to form a liquid premix; (b) blending dry ingredients having at least one of each of a bulking agent, a lipid, a flavoring agent, a disintegrating agent, a binding agent, a surfactant, a preservative, a lubricating agent, and an anti-sticking to form a uniform dry ingredient mixture; (c) blending the premix and the uniform dry ingredient mixture to form a granulated compacted soft-chew mass; (d) sifting the granulated compacted soft-chew mass through at least one sifting screen to form uniform granules of the soft-chew mass; and (d) adding a lubricant or anti sticking agent to the uniform granules of the soft-chew mass and compressing the resulting mixture in a tablet press to from soft-chew tablets.

By the term "active ingredient" or "active agent," it is meant an active pharmaceutical ingredient or nutritional agent. By the term "fluid," it is meant a material that is flowable or malleable. A fluid material may be a viscous liquid, with a viscosity comparable, for example, to water, vegetable oil, honey, or peanut butter.

In an embodiment, two or more mixtures are prepared in the inventive process. A first mixture is a premix containing the active ingredient, and a second mixture is a blend of dry ingredients. The premix and dry ingredient blend may be blended together to form a soft-chew mass.

In an embodiment, the active ingredient is mixed with a vegetable oil to form a premix. The vegetable oil may be, for example, soybean oil, olive oil, flaxseed oil, canola oil, or corn oil.

In an embodiment, this invention provides a unit dosage form for the oral administration of a pharmaceutical agent or nutritional agent to a human or animal, comprising a tablet manufactured according to the processes as disclosed herein, wherein the tablet is chewed and swallowed.

In one embodiment, the nutritional agent or pharmaceutically active ingredient is added to the composition by dry blending.

In an embodiment, the bulking agent is microcrystalline cellulose.

In one embodiment, the nutritional ingredient or pharmaceutically active ingredient may be dissolved, emulsified, or suspended in a non-aqueous solvent before addition. The nutritional or pharmaceutically active ingredient may be soluble, partially soluble, or insoluble in water.

A nutritional agent may include vitamins, minerals, glycosaminoglycan or its active members, amino acids or combination thereof that are useful in human or animal nutrition.

An active pharmaceutical ingredient may include any approved or experimental drug. By "approved," it is meant that the drug is approved for human or veterinary use by a regulatory agency in any country that makes such drug approvals. For example, the pharmaceutically active ingredient may be selected from an anesthetic agent, anthelmintic agent, analgesic agent, steroid, corticosteroid agent, nonsteroidal anti-inflammatory drug (NSAID) agent, antiemetic agent, anti-thyroidal agent, parasiticidal agent, appetite stimulant, antihistamine agent, antifungal agent, antiprotozoal agent, or anti-depressant.

In an embodiment, the nutritional ingredient or active pharmaceutical ingredient may be in granular form, and is coated, or further coated, with a suitable coating. For example, the coating could be a coating polymer that coats and protects the nutritional ingredient or pharmaceutically active agent, or masks an offensive taste and/or offensive odor. In an embodiment, the coating could be a functional coating, e.g. an extended-release coating, delayed-release coating, controlled-release coating, barrier coating, or a combination thereof.

In an embodiment, the nutritional ingredient or pharmaceutically active ingredient could be conjugated with other ingredients, such as cyclodextrins, surfactants, solubility or bioavailability enhancers, etc., to inhibit interactions with other excipients or with the environment, or to promote the chemical stability, improve solubility, enhance bioavailability, or improve the palatability of the nutritional ingredient or pharmaceutically active agent. Similarly, the pharmaceutically active ingredient may be incorporated into a novel drug delivery system, such as microspheres, microcapsules, liposomes, niosomes, nanoparticles, microemulsions, or nanoemulsions to protect the drug or permit organ targeting.

The rate of release of the nutritional or pharmaceutically active ingredient from the chewable formulation may be modulated or controlled by, for example, the use of controlled or sustained release agents (e.g. polymers) or by using excipients (e.g. disintegrants) that promote in rapid release, as appropriate.

In some embodiments a single excipient has more than one function in the formulation of the present invention. For example, propylene glycol and glycerol may be present and have a simultaneous role as a plasticizer, humectants, antimicrobial agents, or any combination of any two or more thereof, in this formulation. Oils, lipids or fats may have a role as a lubricant, plasticizer, binders, or any combination of any two or more thereof. Any suitable excipient may be used.

In an embodiment, the composition of the soft-chewable dosage form includes a lipid that may be a liquid vegetable oil, or a solid hydrogenated vegetable oil. The vegetable oil may be, for example, soybean oil, olive oil, flaxseed oil, canola oil, or corn oil.

In one embodiment, the composition of the soft-chewable dosage unit as defined above, is provided wherein a texturing agent, selected from the group comprising of modified corn starches, polyols, poly(ethylene) oxide, microcrystalline cellulose co-processed with guar gum and the like, is added.

A polyol may include propylene glycol, glycerin, polyethylene glycol and mixtures thereof.

In one embodiment, the chewable formulation includes one or more fillers. A filler may be used to increase the total mass of the chewable formulation to a manageable size or to enhance the flow properties of final powder or granules to be compressed in a rotary tablet press.

In one embodiment, the composition of the soft-chewable dosage form, is provided with a binding agent. The binding agent may be polyethylene glycol. The polyethylene glycol may be admixed to dry ingredients for mixing. The polyethylene glycol may be melted and added to at least one other dry ingredient and mixed to form the uniform dry ingredient mixture.

In an embodiment, the soft-chew tablet of this invention may have at least one active ingredient, and includes a vegetable oil and microcrystalline cellulose in a ratio of about 2:1 to about 1:2.5, w/w, and wherein the tablet is manufactured by compression on a tablet press.

For example, one or more diluents may be used in combination with silicified microcrystalline cellulose. Examples of diluents include starches and their derivatives (e.g. hydrogenated starch hydrosylate), celluloses and their derivatives (e.g. cellulose acetate), protein matrices (soy protein, dextrates, wheat gluten, whey, corn cob, corn gluten), carbohydrates (e.g. maltodextrin, polydextrose), sugars and sugar alcohols (glucose, lactose, fructose, maltose, dextrose, sucrose, maltitol, xylitol, isomalt, mannitol), silicates, calcium phosphates, calcium sulfate, dextrates, kaolin, magnesium carbonate, polymethacrylates, talc, salts (e.g. sodium chloride) or any combination of any two or more thereof.

In an embodiment, the composition includes a starch, or a modified starch, or a mixture of starch and a modified starch.

Diluents may also serve a role in fat or oil absorption, disintegration, and binding, providing nutrition, lubrication or any combination of any two or more thereof. The diluents may also be used for taste masking or modifying texture, for example microcrystalline cellulose co-processed with guar gum and/or modified corn starches.

In one embodiment, the chewable formulation includes one or more binders. Binders improve the binding properties of the compacted mass, to assist the formation of compact dosage units. Any suitable binder known in the art may be used. In one embodiment, the binder is selected from gums such as xanthan gum or guar gum, alginates, celluloses and their derivatives such as methylcellulose or microcrystalline cellulose, fats or lipids, starches and their derivatives, dextrins, celluloses and their derivatives, povidones, silicates, mineral oils, vegetable oils, polymethacrylates, polyethylene oxides, gums, waxes, chitosan, polycarbophil, agar, or carbomers, or any combination of any two or more thereof. In some embodiments, the binder is a dry binder such as povidone.

In an embodiment, the formulation of this invention may include one or more palatability enhancers. Palatability enhancers improve the taste of material that is chewed. Advantageously, palatability enhancers may improve the palatability of soft-chewable formulations comprising bitter, acrid, obnoxious, unpleasant, or otherwise unpalatable nutritional or pharmaceutically active agents.

In one embodiment, the palatability enhancer is a taste masking agent, a flavoring agent, an aroma modifier, or a taste modifier, or any combination of any two or more thereof.

Flavoring agents may be used to improve the palatability of the chewable tablets. Any type of flavoring agent can be used provided it improves the palatability of the product, typically by improving either its taste and/or smell. The use of a flavoring agent may also assist with dose compliance. Flavors can be natural (derived from animal or plant sources), semisynthetic, or artificial. In one embodiment, the flavoring agent is an artificial flavoring agent, semi-synthetic flavoring agent, a natural flavoring agent, or nature identical flavoring agent.

In an embodiment, the formulation of this invention may include liquid components that are absorbed on the surface of a lipid absorbing pharmaceutical ingredient selected from one or more of microcrystalline cellulose, silicified microcrystalline cellulose, and a combination of microcrystalline cellulose and guar gum. The liquid components absorbed on the surface of the lipid absorbing pharmaceutical ingredient may be mixed with the uniform dry ingredient mixture and then sifted again through at least one finer sifting screen to form further finer granules of the soft-chew composition mixture. In an embodiment, a nutritional agent or a pharmaceutically active ingredient is admixed with the liquid components prior to mixing with the lipid absorbing pharmaceutical ingredient.

Plasticizers may be used to the formulation to improve plasticity and malleability of dosage units of the present invention. In one embodiment, a plasticizer may be selected from alcohols, glycols (such as propylene glycol), lanolin, wool fat, liquid paraffin, mineral oil, petrolatum, benzyl phenylformate, chlorobutanol, diethyl phthalate, glycerol, polyethylene glycol, propylene glycol, sorbitol, triacetin, benzyl phenyl formate, dibutyl sebacate, tributyl citrate, triethyl citrate, or any combination of any two or more thereof. Other plasticizers known in the art may also be used.

In one embodiment, the dosage units of this invention may include a non-active ingredient including of one or more of a starch, a polysaccharide, a humectant, a polyol, water-soluble poly(ethylene oxide) resin In one embodiment, the dosage units of this invention may include a humectant. A humectant is used to retain moisture in the dosage unit. A humectant of value in this invention may be selected from sodium and potassium chloride, benzalkonium chloride, aluminum silicate, sodium propionates, sodium and potassium phosphates, sugars, sulfites, hydrogenated starch hydrosylate, etc. Liquid humectants include, but are not limited to, glycols, polyols, sugar alcohols, vegetable oils and mineral oil, hydrogenated vegetable oils, hydrocarbons, triacetin, liquid paraffin, or any combination of any two or more thereof. Other humectants known in the art may also be used.

In one embodiment, the dosage units of this invention may include an antioxidant. An antioxidant inhibits oxidation and may be of benefit as a preservative, or to maintain the chemical stability of an active or inactive ingredient. An antioxidant may be selected from propyl gallate, ascorbic acid and its derivatives, sodium formaldehyde sulfoxylate, malic acid, fumaric acid, editic acid, thiols, polyphenols, sodium EDTA, sodium ascorbate, sodium metabisulfite, butylated hydroxytoluene, butylated hydroxyanisole, butylated hydroxyanisole & butylated hydroxytoluene co-processed with zea mays oil or natural substances such as flavanoids, tocopherols, carotenes, cysteine, or any combination of any two or more thereof. Other antioxidants known in the art may also be used. The antioxidants are generally added to the formulation in amounts of from about 0.01 to about 2.0%, based upon total Weight of the formulation, with about 0.1 to about 1.0% being especially preferred.

In an embodiment, the formulation of this invention may include a preservative selected from the group including parabens (methylparaben and/or propylparaben), benzalkonium chloride, benzethonium chloride, benzoic acid, citric acid, fumaric acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, potassium sorbate, sodium benzoate, sodium propionate, sorbic acid, thimerosal and quaternary ammonium compounds. Other preservatives known in the art may also be used.

In one embodiment, the chewable formulation of this invention may include a non-aqueous solvent, for example glycerin. A non-aqueous solvent may disperse, solubilize or enhance solubilization of the nutritional or pharmaceutically active agent. The non-aqueous solvent may also enhance the binding of the formulation and the consistency and texture of the soft-chewable dosage form.

In one embodiment, the chewable formulation of this invention may include a disintegrating agent. A disintegrating agent may be used to enable the inventive chewable tablets to break down on contact with water, saliva, or gastric fluid in the stomach to quickly release the active ingredient. A disintegrating agent may be selected from povidones, croscarmellose sodium, sodium starch glycollate, celluloses and their derivatives, starches and their derivatives, gelatin, silicon dioxide, or any combination of any two or more thereof. Other disintegrating agents known in the art may also be used. Disintegration may be tested and measured using USP Disintegration Test <701> for uncoated tablets, using water as medium.

In an embodiment, a granulated compacted soft-chew mass is formed, and the mass is dried by equipment using direct or indirect conduction heat applied to a static solid bed, a moving solid bed, or a fluidized solid bed. The granulated mass may be dried at room temperature, for example about 25° C.±10° C. Alternatively, the granulated mass may be dried at a controlled temperature of about 50° C. or less.

In an embodiment, the process of this invention may include sifting, or milling, of dry components or a granulated mass, or a mixture of both through sifting screens with mesh sizes commonly known in the art. Mesh sizes for sifting screens may include Mesh #4 or 5 or 6 or 7 or 8 or 10 or 12 or 14 or 16 or 18 or 20 or 25 or 30 or 35 or 40 or 45 or 50 or 60 or other mesh sizes commonly known in the art. Components may be sifted through at two or more screens with different mesh sizes one after other in gradual or random order of mesh sizes.

In an embodiment, the uniform dry ingredient mixture or the granulated compacted soft-chew mass are sifted through sifting equipment using impaction, attrition, compression or cutting.

In an embodiment, the uniform dry ingredient mixture or the granulated compacted soft-chew mass are uniformly mixed using equipment using diffusion mixing, convection mixing or pneumatic mixing.

In an embodiment, the process of this invention may employ pre-compression force applied to the granulated compacted soft-chew mass before application of main compression force for compression of soft-chews.

In an embodiment, the granulated compacted soft-chew mass is fed into a compression die by gravity feed, power assisted feed, by centrifugal force, or by compression coating.

In an embodiment, the soft-chew tablets of this invention may incorporate an abuse-deterrent technology, which can include one or more of high-melting-point excipients that resist heating and injecting; taste modifiers that resist covert administration, snorting (ingestion of a powdered material through the nose) and dose dumping (extraction of active pharmaceutical ingredients (API) from tablets); water insoluble excipients that resist extraction and drink adulteration; waxy excipients that resist snorting; viscosity modifiers that resist dissolution, injection and dose dumping; low-density excipients that resist drink adulteration; and dyes, that resist adulteration.

The breaking force of tablets is commonly called hardness in the pharmaceutical literature. The term crushing strength is also frequently used to describe the resistance of tablets to the application of a compressive load.

The measure of the mechanical integrity of tablets is their breaking force or hardness, which is the force required to cause them to fail (i.e., break) in a specific plane. Various equipment is used for hardness measurements, for example a Monsanto Hardness Tester, Stokes Hardness tester, Pfizer Hardness Tester, Strong-Cobb Hardness Tester, or Schleuniger Hardness tester. Tablet hardness can be expressed using various units depending on the equipment used for hardness measurement. The units for tablet hardness measurement are newtons, pounds, Strong-Cobb units, and kiloponds.

For the hardness measurements for exemplarily examples in this invention, a Schleuniger Hardness tester was used, and hardness was measured in kiloponds or newtons. This apparatus has two parallel platens between which a tablet is placed. A load is applied and the value of the hardness is measured. The platen faces are polished smooth and precision-ground perpendicularly to the direction of movement. Perpendicularity is preserved during platen movement, and the mechanism is free of any bending or torsion displacements as the load is applied. The contact faces are larger than the area of contact with the tablet.

In one embodiment, the chewable formulation of this invention includes dosage units which have hardness of less than 2 kilopond, preferably less than 1 kilopond, and more preferably has no measurable hardness when measured with a tablet hardness tester.

In an embodiment, the chewable formulation of this invention includes dosage units with hardness less than 3.0 Strong Cobb units, preferably less than 1.5 Strong Cobb units, or more preferably no measurable hardness when measured with a tablet hardness tester.

In an embodiment, the chewable formulation of this invention includes dosage units with hardness less than 5.0 pound, preferably less than 2.5 pound, or more preferably no measurable hardness when measured with a tablet hardness tester.

In an embodiment, the chewable formulation of this invention includes dosage units with hardness less than 20.0 newtons, preferably less than 10 newtons, or more preferably no measurable hardness when measured with a tablet hardness tester.

A friability value of about 1 percent or less (when measured as per USP test) is desirable for tablets in order for them to withstand the stress of handling during production, packaging, and transport.

In one embodiment the formulation comprises of dosage units with friability less than 1%, preferably less than 0.5%, or more preferably less than 0.1% for 100 rotations (per USP), or 200 rotations, or 300 rotations.

For traditional tablet compression using rotary tablet press, tablet hardness is traditionally kept 3 kilopond or more. As dosage form size increases, compression force is increased to produce tablet with even higher hardness.

For tablets having hardness 5 kilopond or less, a high order of tablet rejection results because of stress during production, packaging, and transport. For such tablets tablet friability is generally between 0.1 and 1.0% when performed as per USP test.

As tablet hardness decreases, tablet friability generally increases. But the instant inventors have unexpectedly found that for exemplarily formulations herein, soft-chewable tablets with hardness less than 2 kilopond or lower, friability remains less than 1%, preferably less than 0.5%, more preferably less than 0.1% for 100 rotations (per USP); 200 rotations or 300 rotations.

In one embodiment, the soft-chewable tablet maintains a characteristic selected from chewiness, hardness, compression energy, adhesion, cohesiveness, springiness, and modulus, and any combination of any two or more thereof (when measured by the texture analyzer as per procedure for example 1) sufficient to provide a chewable texture.

In one embodiment, the dosage unit of this invention (e.g. soft-chew) has a weight between about 0.1 and about 10 g. In one embodiment, the dosage unit has a weight between about 0.5 and about 4.0 g. In one embodiment, the dosage unit has a weight between about 0.1 g and about 3.0 g. In another embodiment, the weight of the dosage unit is between about 0.1 g and about 2.0 g.

In an embodiment, weight of the dosage unit can be between about 0.1 and about 1.0 g; or between about 1.1 g and about 2.0 g; or between about 2.1 g and about 3.0 g; or between about 3.1 g and about 4.0 g; or between about 4.1 g and about 5.0 g.

In an embodiment, the dosage unit (e.g. soft-chew) of this invention can have an imprint on at least one surface of the dosage unit. In a specific embodiment this imprint can be on the top surface of the dosage unit. Such imprint can be e.g. letters, numbers, logos or symbols etc. An imprint can also be on the bottom surface.

In one embodiment, the dosage unit has a score or groove on one of the surfaces. This cross score has the effect that it facilitates the dividing of the dosage unit and allows more exact dosing of the active pharmaceutical ingredient according to the body weight, and/or age of the patient.

Such dosage units can have different weights, dimensions and shapes that can be adapted to the weight and need of the target patient population to allow accurate dosing. Dosage forms can be to different weights, dimensions and shapes known in the art. For example, the soft-chew tablets of this invention can be round, capsule-shaped, or have a modified shape.

The soft-chewable tablets of this invention can be packaged as bulk primary packaging, or as singular unit primary packaging.

EXAMPLES

Example 1

TABLE 1

| Ingredients | % w/w |
| --- | --- |
| Active | |
| Placebo Active | 3.0 |
| Granulation Aid | |
| Soybean Oil | 15.0 |
| Zea Mays (corn) Oil & butylated hydroxyanisole (BHA) & butylated hydroxy toluene (BHT) | 0.1 |
| Glycerin | 19.0 |
| Intragranular Addition | |
| Microcrystalline Cellulose | 21.0 |
| Pregelatinized Corn Starch | 5.0 |

TABLE 1-continued

| Ingredients | % w/w |
| --- | --- |
| Extragranular Addition | |
| Pregelatinized Corn Starch | 3.0 |
| Beef Flavor | 19.0 |
| Sodium Lauryl Sulfate | 0.2 |
| Poly(ethylene) Oxide | 1.0 |
| Maltodextrin | 3.0 |
| Modified Corn Starch | 3.0 |
| Crosscarmellose Sodium | 3.7 |
| Color | 0.01 |
| Polyethylene Glycol 3350 | 2.0 |
| Flow Aid | |
| Magnesium Stearate | 1.0 |
| Colloidal Silicon Dioxide | 1.0 |
| Total | 100.0 |

Procedure

1. Two methods were employed using the formulation summarized in Table 1. In the first method, a placebo active was added as part of granulation aid components, and in the second method placebo active was added as part of extra-granular addition, remaining procedure was same for both methods.
2. The intragranular ingredients and the active were passed through a sifting screen followed by uniform mixing.
3. The extragranular ingredients were passed through a sifting screen followed by uniform mixing.
4. Granulation aid components were added to the intragranular blend and mixed thoroughly until uniformly mixed, followed by melting polyethylene glycol 3350 and quickly adding this to granulated mass, followed by uniform mixing.
5. The granulated mass from step 4 was passed through a sifting screen to form uniform granules.
6. The extragranular blend from step 3 was added to screened granules from step 5, followed by uniform mixing.
7. Blended granules from step 6 were passed through a sifting screen.
8. Magnesium stearate and colloidal silicon dioxide mixed with small amount of granules from step 6 and passed sifting screen.
9. The milled (sifted) components from step 8 were added to granules from step 6 followed by uniform mixing followed by compressing on a rotary tablet press using 18 mm×18 mm rounded square punch.

Texture Analysis was performed using CT3 Texture Analyzer (Brookfield Engineering) using a TA3/100 probe and 25,000 g load cell and 5 g trigger load, over 4 mm using 2 mm/s test speed and using a data rate of 100 points/second. Load peaks were applied at 2, 9, and 10 seconds. The results are plotted in FIG. 1.

TABLE 2

Example 1: Tablet Characterization and Comparison to Marketed Soft-chewable Tablet Compared to Example 1

| Test Parameters | Marketed Soft-chewable Tablet | Example 1 |
| --- | --- | --- |
| Formulation Approach | Unconventional Molding Method | Conventional Tablet Press Compression Method |

TABLE 2-continued

Example 1: Tablet Characterization and Comparison to Marketed Soft-chewable Tablet Compared to Example 1

| Test Parameters | Marketed Soft-chewable Tablet | Example 1 |
|---|---|---|
| Physical Characterization | | |
| Weight(g) | 3.600-3.750 | 3000 |
| Shape | Trapezoidal | Square |
| Color | Multiple Strengths with different colors | Yellowish Brown |
| Top[W(mm), L(mm)] | 16.10, 17.40 | 18 × 18 |
| Bottom [W(mm), L(mm)] | 17.80, 18.60 | 18 × 18 |
| Thickness (mm) | 9.20-9.60 | 8.00-9.00 |
| Disintegration Time (min) | 20-26 | 10-15 |
| Tablet Hardness (kp) | 0 | 0 |
| Tablet Friability (%) | 0 | 0 |
| Soft-chew Characterization [1] | | |
| Hardness | 3000-3900 g | 3698.00 g-3866.00 g |
| Deformation at Hardness | 3.95-4.00 mm | 1.78 mm-3.58 mm |
| Adhesiveness | 0.00-0.20 mJ | 0.00 mJ-0.10 mJ |
| Cohesiveness | 0.30-0.34 | 0.00-0.15 |
| Gumminess | 1100.00 g-1450.00 g | 4.00 g-546.00 g |
| Chewiness | 24.40 mJ-93.70 mJ | 0.00-42.70 mJ |

[1] Using CT3 Texture Analyzer

Example 2 (Conventional Hard Chewable Tablet)

TABLE 3

| Ingredients | % |
|---|---|
| Step 1 Ingredients | |
| Carprofen | 5.00 |
| Artificial Beef Flavor | 20.0 |
| Silicified Microcrystalline Cellulose | 17.95 |
| Polycarbophil | 2.50 |
| Polyethylene Glycol 3350 | 6.00 |
| Microcrystalline Cellulose & Guar Gum | 3.00 |
| Pregelatinized Corn Starch | 24.0 |
| Lactose Monohydrate | 15.0 |
| Crosscarmellose Sodium | 2.50 |
| Step 2 Ingredients | |
| Color 1 | 0.03 |
| Color 2 | 0.02 |
| Talc | 2.00 |
| Magnesium Stearate | 2.00 |
| Total | 100 |

Procedure

1. All step 1 ingredients were individually weighed and passed through a sifting screen and uniformly mixed.
2. The step 2 ingredients were mixed along with small quantity of pre-mix from step 1.
3. The ingredients from step 2 were added to the remaining pre-mixed ingredients from step 1 and mixed for uniform mixing for 2-3 minutes and further subjected to compression on rotary tablet press for 500 mg fill weight.

Examples 3 and 4

TABLE 4

Examples 3 and 4

| Ingredients | Example 3 % w/w | Example 4 % w/w |
|---|---|---|
| Active | | |
| Carprofen | 0.84 | 3.34 |
| Granulation Aid | | |
| Soybean Oil | 16.00 | 9.00 |
| Zea Mays Oil & BHA & BHT | 0.10 | 0.10 |
| Glycerin | 20.00 | 13.00 |
| Polyethylene Glycol 600 | — | 9.00 |
| Povidone K 30 | 2.00 | 2.00 |
| Intragranular Addition | | |
| Polycarbophil | 0.30 | — |
| Silicified Microcrystalline Cellulose | 16.06 | 18.66 |
| Pregelatinized Corn Starch | 7.00 | 7.00 |
| Calcium Sulfate Dihydrate | 1.30 | 2.50 |
| Artificial Beef Flavor | 8.00 | 15.00 |
| Crosscarmellose Sodium | 2.50 | 2.50 |
| Polyethylene Glycol 600 | — | — |
| Polyethylene Glycol 3350 | 2.00 | — |
| Extragranular Addition | | |
| Pregelatinized Corn Starch | 4.00 | 5.00 |
| Artificial Beef Flavor | 10.00 | 3.00 |
| Sodium Lauryl Sulfate | 0.20 | 0.20 |
| Poly(ethylene) Oxide | 1.00 | 1.00 |
| Modified Corn Starch | 3.00 | — |
| Crosscarmellose Sodium | 2.50 | 2.50 |
| Calcium Sulfate Dihydrate | 1.70 | 1.70 |
| Lactose Monohydrate | 1.50 | 4.50 |
| Total | 100.00 | 100.00 |

Procedure: Example 3

1. The active, soybean oil and Zea Mays Oil & BHA & BHT are weighed accurately and uniformly mixed to form a dispersion.
2. Simultaneously, a dispersion was prepared by adding povidone to glycerin and properly mixing.
3. Intra granular dry ingredients were passed through a sifting screen followed by uniform mixing.
4. Dispersions from step 1 and step 2 were used as granulation aid, adding them one after another to pre-mixed ingredients from step 3.
5. The formed doughy mass was passed through a sifting screen to get wet granules.
6. Extragranular ingredients were passed through a sifting screen followed by uniform mixing.
7. Approximately half the quantity of the extragranular blend from step 6 was added to the wet granules formed in step 5 and uniformly mixed.
8. The formed slightly dry granular mass was further passed through sifting screen to obtain granules.
9. The formed granules are uniformly mixed with remaining quantity of extra granular blend from step 6 and further subjected to compression on rotary tablet press using 18 mm×18 mm rounded square punch for 3.0 gram target fill weight.

Procedure: Example 4

1. Active, soybean oil and Zea Mays Oil & BHA & BHT are weighed accurately and uniformly mixed to form a dispersion.

Figure 2:
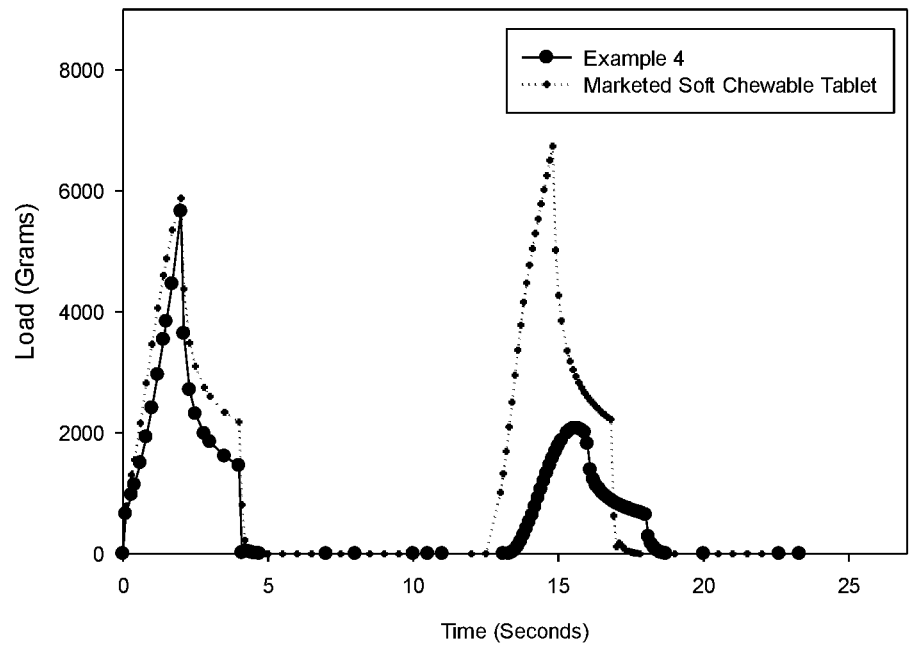
FIG. 2. Is a plot of the texture characterization and comparison to marketed soft-chewable tablet for data in Example 4, showing load peaks applied at 2, and 15 seconds.

2. Simultaneously, a dispersion was prepared by adding Povidone and Polyethylene Glycol 600 to Glycerin and properly mixing.
3. The Intragranular dry ingredients were mixed together and passed through a sifting screen.
4. The extragranular dry ingredients were mixed together and passed through a sifting screen.
5. The pre-mix from step 3 was added to a Rapid Mixer Granulator (RMG) bowl of appropriate size and mixed for 2 minutes with 60 rpm impeller speed.
6. The Dispersion from step 1 was added slowly in about 1 minute and mixed further for 4 minutes with 60 rpm impeller speed and 150 rpm chopper speed.
7. The dispersion from step 2 was added slowly in about 2 minute with 50 rpm impeller speed and 150 rpm chopper speed.
8. The formed doughy mass was passed through a sifting screen to get wet granules.
9. Approximately half the quantity of the extragranular blend from step 4 was added to the wet granules formed in step 8 and uniformly blended.
10. The formed slightly dry granular mass was further passed through a sifting screen to get granules.
11. The formed granules had a Loss on Drying (LOD) value of 7.76% w/w @ 105° C. in 9:35 minutes.
12. The formed granules are uniformly mixed with the remaining quantity of the extragranular blend from step 4 and further subjected to compression on rotary tablet press using 18 mm×18 mm rounded square punch for 3.0 gram target fill weight.
13. The compressed tablets exhibited tablets hardness of 0 newton or kilopond when measured using conventional hardness tester and had tablet friability of 0.02% w/w.
14. Texture Analysis was performed using CT3 Texture Analyzer using TA/RT/KIT probe and 25,000 g load cell and 510 g trigger load, over 4 mm using 2 mm/s test speed and using data rate of 10 points/second. Load peaks were applied at 2 and 15 seconds. The results are plotted in FIG. 2.

TABLE 5

Example 2, 3 & 4 Tablet Characterization:

| Test Parameters | Example 2 | Example 3 | Example 4 |
|---|---|---|---|
| Weight(g) | 0.500 | 3.0 | 3.0 |
| Shape | Square | Square | Square |
| Color | Light Brown | Yellow-Brown | Yellow-Brown |
| Dimension (mm) | — | 18 × 18 | 18 × 18 |
| Thickness (mm) | 4-5 | 7-8 | 8.00-9.00 |
| Disintegration Time (min) | | 10-15 | 20-21 |
| Tablet Hardness (Kp) | 16-18 | 0 | 0 |
| Tablet Hardness (N) | 170 N | — | 0 |
| Tablet Friability (% w/w) | — | 0 | 0.02 |
| LOD @ 105° C. | 6-7 | — | 7-8 |

In Vitro Analysis (Multimedia Dissolution Testing)

TABLE 6

A] Dissolution in 0.1N HCl

Dissolution Medium
0.1N HCl, USP II Apparatus, 900 ml, 100 rpm

| Time Points (Minutes) | Reference Drug (Hard Chew) | Example 2 (Hard Chew) | Marketed Soft-chew | Example 3 Prototype Soft-chew |
|---|---|---|---|---|
| 5 | 4.2 | 5 | 17 | 12.5 |
| 15 | 8.8 | 10 | 28 | 24.0 |
| 30 | 9.4 | 15 | 33 | 32.0 |
| 45 | 9.9 | 13 | 37 | 32.1 |
| 60 | 11.6 | 13 | 34 | 33.2 |
| 90 | 11.9 | 18 | 35 | 30.5 |
| 120 | 12.7 | 15 | 36 | 30.6 |

Figure 3:
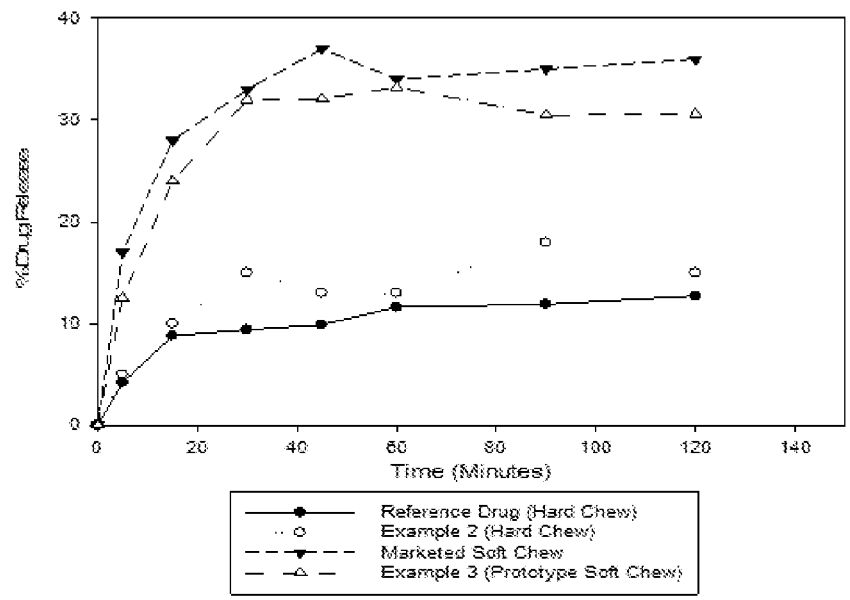
FIG. 3. Is a plot of the dissolution vs. time in 0.1 N HCl, USP II apparatus, 900 ml, 100 rpm for data in Table 6.

The data in Table 6 is presented graphically in FIG. 3.

TABLE 7

B] In Acetate Buffer pH 4.5

Dissolution Medium
Acetate Buffer pH 4.5, USP II Apparatus, 900 ml, 100 rpm

| Time Points (Minutes) | Reference Drug (Hard Chew) | Example 2 (Hard Chew) | Marketed Soft-chew | Example 3 Prototype Soft-chew |
|---|---|---|---|---|
| 5 | 5.8 | 13 | 21 | 18.0 |
| 15 | 14.5 | 24 | 41 | 37.5 |
| 30 | 19.4 | 32 | 53 | 51.4 |
| 45 | 21.2 | 33 | 55 | 54.4 |
| 60 | 24.0 | 33 | 56 | 54.1 |
| 90 | 25.5 | 34 | 56 | 51.5 |
| 120 | 25.5 | 34 | 57 | 53.0 |

Figure 4:
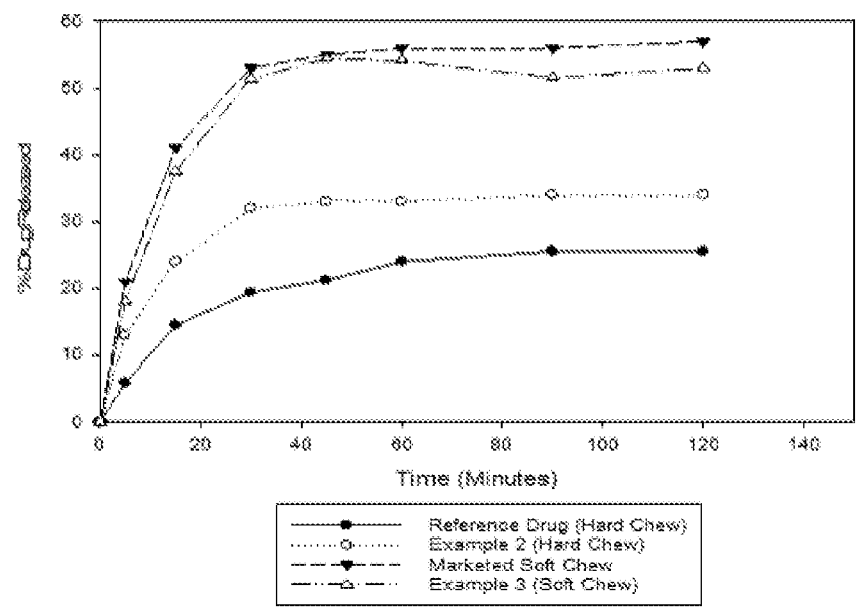
FIG. 4. Is a plot of the percent drug release vs. time in acetate buffer, USP II, 900 ml, 100 rpm for data in Table 7.

The data in Table 7 is presented graphically in FIG. 4.

TABLE 8

C] Dissolution in Phosphate Buffer pH 7.5

Dissolution Medium
Phosphate Buffer pH 7.5, USP II Apparatus, 900 ml, 100 rpm

| Time Points (Minutes) | Reference Drug (Hard Chew) | Example 2 (Hard Chew) | Marketed Soft-chew | Example 3 Prototype Soft-chew |
|---|---|---|---|---|
| 5 | 23.8 | 26.00 | 25.0 | 22.0 |
| 15 | 59.2 | 68.00 | 66.9 | 55.0 |
| 30 | 90.8 | 92.00 | 91.1 | 87.0 |
| 45 | 93.2 | 92.00 | 95.3 | 96.0 |
| 60 | 93.6 | 92.00 | 95.3 | 97.0 |
| 90 | 93.7 | 92.00 | 95.3 | 97.0 |
| 120 | 94.1 | 93.00 | 95.3 | 97.0 |

Figure 5:
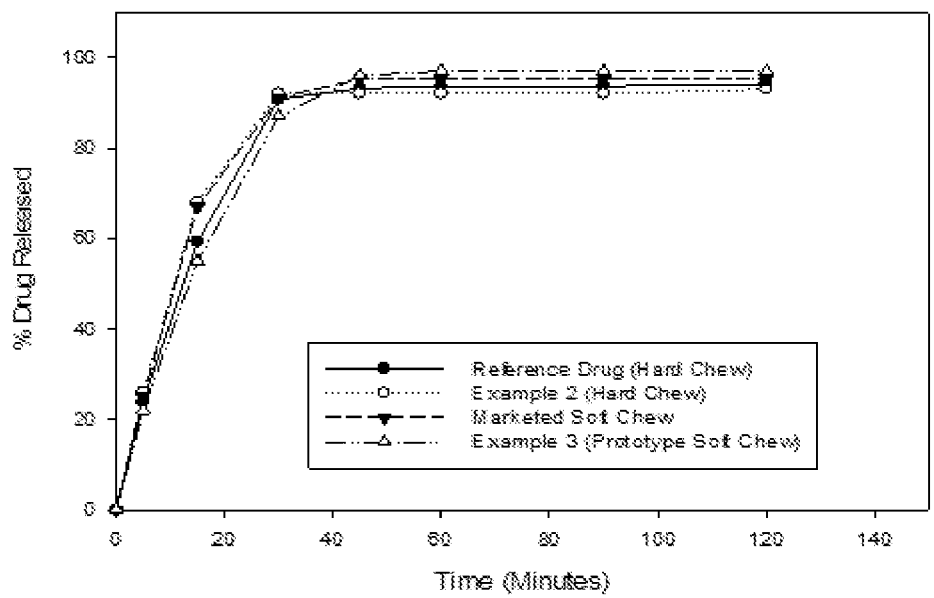
FIG. 5. Is a plot of the percent drug release vs. time in phosphate buffer, pH 7.5, USP II apparatus, 900 ml, 100 rpm for data in Table 8.

The data in Table 8 is plotted in FIG. 5.

Examples 5-8

TABLE 9

Examples 5-8

| Formulation Ingredients | Example 5 % w/w | Example 6 % w/w | Example 7 % w/w | Example 8 % w/w |
|---|---|---|---|---|
| Active | | | | |
| Cefpodoxime Proxetil | 13.50 | — | — | — |
| Enrofloxacin | — | 4.54 | — | — |

TABLE 9-continued

Examples 5-8

| Formulation Ingredients | Example 5 % w/w | Example 6 % w/w | Example 7 % w/w | Example 8 % w/w |
|---|---|---|---|---|
| Pimobendan | — | — | 0.08 | — |
| Deracoxib | — | — | — | 3.34 |
| Granulation Aid | | | | |
| Soybean Oil | 7.00 | 9.00 | 10.00 | 15.00 |
| Zea Mays Oil & BHA & BHT | 0.10 | 0.10 | 0.10 | 0.10 |
| Glycerin | 20.00 | 13.00 | 12.00 | 19.50 |
| Polyethylene Glycol 600 | 3.00 | 9.00 | 10.20 | — |
| Povidone K 30 | 2.00 | 2.00 | 2.00 | 2.00 |
| Color | — | — | 0.01 | 0.02 |
| Intragranular Addition | | | | |
| Polycarbophil | — | — | — | 0.25 |
| Lactose Monohydrate | — | — | — | — |
| Sodium Carboxymethylcellulose | 20.00 | — | — | — |
| Silicified Microcrystalline Cellulose | 3.85 | 18.15 | 18.71 | 15.59 |
| Sodium Lauryl Sulfate | 1.50 | — | — | — |
| Pregelatinized Corn Starch | 2.00 | 7.00 | 7.00 | 8.00 |
| Calcium Sulfate Dihydrate | — | 2.50 | 2.50 | 2.50 |
| Artificial Beef Flavor | 15.00 | 15.00 | 15.00 | 15.00 |
| Crosscarmellose Sodium | 2.00 | 3.50 | — | 1.50 |
| Polyethylene Glycol 600 | — | — | 2.50 | 1.00 |
| Color | — | — | — | — |
| Polyethylene Glycol 3350 | — | — | — | — |
| Extragranular Addition | | | | |
| Pregelatinized Corn Starch | — | 4.00 | 5.00 | 5.00 |
| Artificial Beef Flavor | 3.00 | 3.00 | 3.00 | 3.00 |
| Citric Acid | — | — | — | — |
| Sodium Carboxymethylcellulose | 5.00 | — | — | — |
| Sodium Lauryl Sulfate | — | 0.20 | 0.30 | 0.20 |
| Poly(ethylene) Oxide | — | 1.00 | 1.00 | 1.00 |
| Color | 0.05 | — | — | — |
| Modified Corn Starch | — | — | — | — |
| Crosscarmellose Sodium | 2.00 | 1.50 | 2.50 | 5.00 |
| Calcium Sulfate Dihydrate | — | 2.01 | 1.70 | 1.00 |
| Lactose Monohydrate | — | 4.50 | 6.50 | 1.00 |
| Total | 100.00 | 100.00 | 100.00 | 100.00 |

Procedure: Example 5
1. Soybean oil and Zea Mays Oil & BHA & BHT are weighed accurately and uniformly mixed to form a dispersion.
2. Simultaneously, a dispersion is prepared by adding Polyethylene Glycol 600 to Glycerin and properly mixing.
3. Cefpodoxime Proxetil (Active) was part of the intragranular addition. All intragranular dry ingredients were mixed uniformly and passed through sifting screen.
4. The dispersions from step 1 and step 2 are used as granulation aid, adding them one after another to the pre-mixed ingredients from step 3.
5. The formed doughy mass was passed through a sifting screen to get wet granules.
6. The extragranular ingredients were mixed uniformly and passed through a sifting screen.
7. Approximately half the quantity of the extragranular blend from step 6 was added to the wet granules formed in step 5 and mixed uniformly.
8. The formed slightly dry granular mass was passed through sifting screen to get granules.
9. The formed granules were mixed uniformly with remaining quantity of extragranular blend and further subjected to compression on rotary tablet press using 15.3 mm×15.3 mm rounded square punch for 2000 mg fill weight & 12.3×12.3 mm rounded square for 1000 mg fill weight separately.

TABLE 10

Comparative Dissolution in Glycine Buffer pH 3.0

Dissolution Medium
Glycine Buffer pH 3.0, USP II Apparatus, 900 ml, 75 rpm

| Time Points (Minutes) | Reference Drug, 100 mg (Hard Chew) | Example 5 (1000 mg) (soft-chew) | Reference Drug, 200 mg (Hard Chew) | Example 5 (2000 mg) (soft-chew) |
|---|---|---|---|---|
| 5 | 79.8 | 50.8 | 77.1 | 43.2 |
| 15 | 99.9 | 95.8 | 92.3 | 86.4 |
| 30 | 102.2 | 103.3 | 98.0 | 99.0 |
| 45 | 101.00 | 104.8 | 98.40 | 103.0 |

Figure 6:
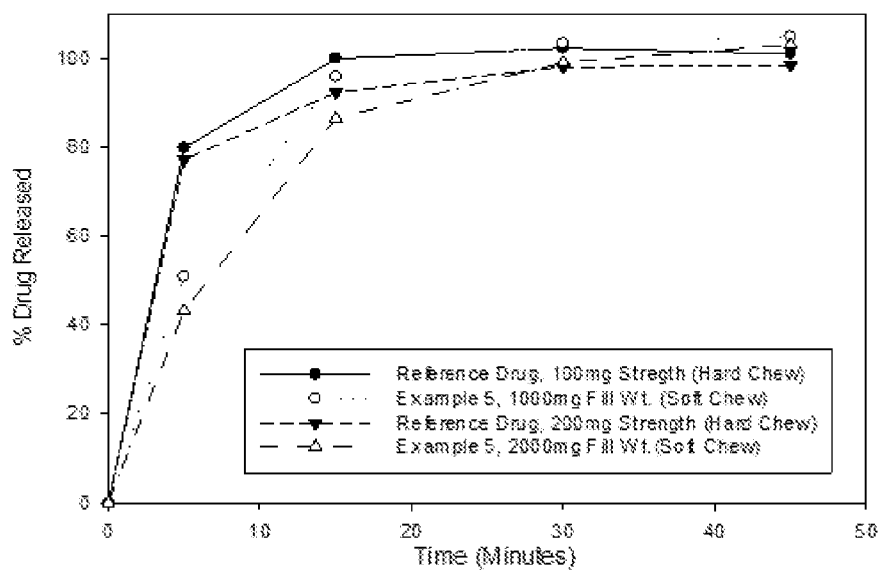
FIG. 6. Is a plot of the comparative dissolution of data in Table 10, glycine buffer pH 3.0, USP II apparatus, 900 ml, 75 rpm.

The data in Table 10 is plotted in FIG. 6.

Procedure: Examples 6-8
1. The active, soybean oil and Zea Mays Oil & BHA & BHT were uniformly mixed to form a dispersion.
2. Simultaneously, a dispersion was prepared by weighing the remaining granulation aid ingredients followed by properly mixing.
3. Intra granular dry ingredients were uniformly mixed and passed through a sifting screen.
4. The dispersions from step 1 and step 2 were used as a granulation aid, adding them one after another to pre-mixed ingredients from step 3.
5. The formed mass was passed through sifting screens to get wet granules.
6. The extragranular ingredients were mixed uniformly and passed through a sifting screen.
7. Approximately half the quantity of the extragranular blend from step 6 was added to the wet granules formed in step 5 and mixed uniformly.
8. The formed slightly dry granular mass was passed through a sifting screen to obtain granules.
9. The formed granules are uniformly mixed with remaining quantity of extra granular blend and further subjected to compression on rotary tablet press.

TABLE 11

Comparative Dissolution in Citrate Buffer pH 4.0

Dissolution Medium
Citrate Buffer pH 4.0, USP II Apparatus, 900 ml, 100 rpm

| Time Points (Minutes) | Reference Drug, (Hard Chew) | Example 6 (soft-chew) |
|---|---|---|
| 5 | 64.9 | 95.2 |
| 10 | 96.9 | 97.2 |
| 15 | 98.7 | 97.7 |
| 30 | 99.2 | 96.6 |
| 45 | 98.8 | 98.6 |

Figure 7:
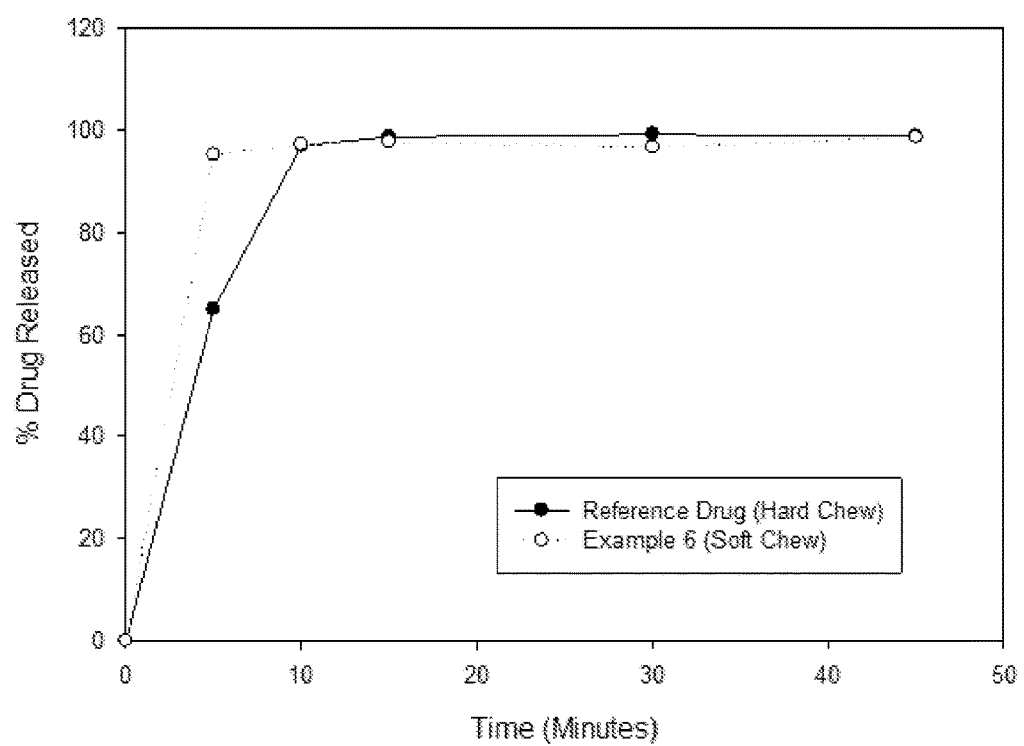
FIG. 7. Is a plot of the percent drug release v/s time in citrate buffer pH 4.0, USP II apparatus, 900 ml, 100 rpm for data in Table 11.

The data in Table 11 is plotted in FIG. 7.

The invention claimed is:
1. A process for the manufacture of a compressed soft-chew semi-plastic unit dosage form, manufactured without molding or extrusion, for the oral administration of active pharmaceutical agents or nutritional agents comprising the steps of:
   a. forming a fluid premix comprising 5% to 20% w/w vegetable oil of the total weight of the dosage form and 5% to 20% w/w glycerin of the total weight of the dosage form;

b. blending granulation ingredients comprising 3.0% to 25% w/w of microcrystalline cellulose, or silicified microcrystalline cellulose and at least one other excipient to form a granulation ingredient mixture;

c. wherein at least one active pharmaceutical agent or nutritional agent is added to the fluid premix or granulation ingredient mixture;

d. blending the fluid premix and the granulation ingredient mixture to form a soft-chew mass;

e. a sifting the soft-chew mass to form granules of the soft-chew mass;

f. adding a lubricant or anti-sticking agent to the granules of the soft-chew mass and compressing the resulting mixture on a tablet press to form a soft-chew semi-plastic unit dosage form, wherein the resulting dosage forms have a hardness of less than 2 kp when tested with a conventional tablet hardness tester and a friability of less than 1.0% at 100 rotations.

2. The process of claim 1, wherein the compressed soft-chew semi-plastic unit dosage form disintegrates in less than 60 minutes according to the USP disintegration test <701> using water as the medium.

* * * * *